United States Patent [19]

Friary

[11] Patent Number: 5,070,086
[45] Date of Patent: Dec. 3, 1991

[54] IMIDAZO- AND PYRIMIDO-QUINOLINE, NAPHTHYRIDINE AND PYRIDOPYRAZINE COMPOUNDS

[75] Inventor: Richard Friary, West Orange, N.J.

[73] Assignee: Schering Corporation, Kenilworth, N.J.

[21] Appl. No.: 499,473

[22] PCT Filed: Dec. 21, 1988

[86] PCT No: PCT/US88/04527
§ 371 Date: Jun. 15, 1990
§ 102(e) Date: Jun. 15, 1990

Related U.S. Application Data

[63] Continuation-in-part of Ser. No. 137,306, Dec. 23, 1987, abandoned.

[51] Int. Cl.$^5$ .................. C07D 471/14; C07D 239/00; C07D 221/00; A61K 31/00
[52] U.S. Cl. .................... 514/183; 546/64; 546/82; 544/182; 544/249; 544/250; 544/251; 544/238; 544/247; 544/343; 544/346; 548/324; 540/471; 540/555; 540/559; 514/220; 514/219; 514/242; 514/248; 514/250; 514/257; 514/267; 514/287
[58] Field of Search .................. 546/64, 82; 544/182, 544/249, 250, 251, 238, 247, 343, 346; 548/324; 540/471, 555, 559; 514/183, 220, 242, 248, 250, 257, 267, 287, 293, 393, 252, 219

[56] References Cited

U.S. PATENT DOCUMENTS

| 3,578,677 | 5/1971 | Sulkowski | 548/524 |
|---|---|---|---|
| 3,598,823 | 8/1971 | Hardtmann | 540/559 |
| 3,657,221 | 4/1972 | Sulkowski | 548/324 |
| 4,186,200 | 1/1980 | Kubo et al. | 424/256 |
| 4,251,533 | 2/1981 | Kubo et al. | 424/256 |
| 4,284,778 | 8/1981 | Kubo et al. | 546/115 |
| 4,288,438 | 9/1981 | Kubo et al. | 424/251 |
| 4,404,380 | 9/1983 | Temple, Jr. | 540/539 |
| 4,647,301 | 3/1987 | Los | 546/82 |
| 4,725,596 | 2/1988 | Frisry et al. | 514/214 |

FOREIGN PATENT DOCUMENTS

| 1951516 | 4/1971 | Fed. Rep. of Germany | 546/82 |
|---|---|---|---|
| 2731982 | 1/1978 | Fed. Rep. of Germany | 546/82 |
| 1319493 | 6/1973 | United Kingdom | 544/247 |

OTHER PUBLICATIONS

Chemical Abstracts, vol. 90, No. 16, Abstract No. 127,546w, Apr. 16, 1979.
Justus Liebigs Annalen Der Chemie, vol. 729, (1969), pp. 83–96.
Indian Journal of Chemistry, vol. 8, Jul. 1970, pp. 663–664.
Chemical Abstracts, vol. 92, No. 7, Abstracts No. 58,685t, 2/18/90, p. 666.
Helvetica Chimica Acta, vol. 71, No. 1, 1988, pp. 77–92.
Mutschler, E.: Arzneimittelwirkungen-Lehrbuch Der Pharmakologia und Toxikologie 5th Edition (1986) pp. 183–187 & 373–378; English translation provided.

*Primary Examiner*—Alan L. Rotman
*Assistant Examiner*—Zinna Northington Davis
*Attorney, Agent, or Firm*—Edward H. Mazer; James R. Nelson; Steinar V. Kanstad

[57] ABSTRACT

Imidazo- and pyrimido-quinoline, naphthyridine and pyridopyrazine compounds, methods of making said compounds and their use as anti-allergy, antiinflammatory and/or agents for the treatment of hyperproliferative skin disease are disclosed.

10 Claims, No Drawings

IMIDAZO- AND PYRIMIDO-QUINOLINE, NAPHTHYRIDINE AND PYRIDOPYRAZINE COMPOUNDS

CROSS REFERENCE TO RELATED APPLICATIONS

This application is a continuation-in-part of U.S. Ser. No. 137,306 filed Dec. 23, 1987, now abandoned.

The present invention relates to imidazo- and pyrimido-quinoline, naphthyridine and pyridopyrazine compounds and their use as anti-allergy and anti-inflammation agents and in the treatment of hyperproliferative skin disease.

One aspect of the invention relates to compounds having the structural formula I

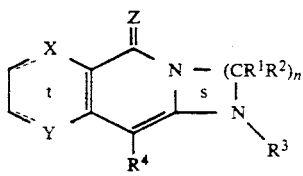

or a pharmaceutically acceptable salt or solvate thereof, wherein:
the dotted lines --- in ring t either both represent double bonds or such double bonds are absent;
X and Y each independently represent $CH_2$ or $NR^3$ if the dotted line attached thereto does not represent a double bond or CH or N if the dotted line attached thereto represents a double bond;
Z represents O, S or $NR^5$;
n of ring s represents an integer 2, 3, 4, or 5;
$R^1$ and $R^2$ may be the same or different and each $R^1$ and each $R^2$ independently represents H or alkyl or two $R^1$ and $R^2$ groups on the same or different carbon atoms may together represent a carbocyclic ring having from 5 to 8 carbon atoms;
each $R^3$ independently represents H, alkyl, aralkyl, heteroarylalkyl, acyl, aroyl or heteroaroyl;
$R^4$ represents H, alkyl, aryl, aralkyl or heteroaryl; and
$R^5$ represents H, alkyl, aryl, heteroaryl, aralkyl, heteroarylalkyl, acyl, aroyl or heteraroyl;

Preferred embodiments of the invention include compounds where:
Z is O or S;
$R^3$ is H or alkyl;
$R^4$ is unsubstituted or mono or disubstituted phenyl or naphthyl where the substituents are selected from alkyl, alkoxy and halogen; and n is 2 or 3.

In preferred embodiments of the compounds of formula I, both dotted lines in ring t represent double bonds and Y preferably is N and X preferably is CH. Z preferably represents O and $R^1$ and $R^2$ are both preferably H. $R^3$ is preferably H and n is preferably 2. $R^4$ is preferably a phenyl, substituted phenyl, naphthyl, or substituted naphthyl group, e.g. 4-methyl, 2-, 3- or 4-methoxy-phenyl, 2-, 3- or 4-chlorophenyl, 3,4-dichlorophenyl, etc.

Another aspect of the invention involves a pharmaceutical composition comprising at least one compound of formula I as defined above in combination with a pharmaceutically acceptable carrier.

The compound of formula I as defined above may be used to treat allergy, inflammation and hyperproliferative skin disease in mammals by administering an effective amounts of such compounds to the mammals.

Certain compounds of the invention may exist in isomeric forms. The invention contemplates all such isomers both in pure form and in admixture, including racemic mixtures.

The compounds of the invention of formula I can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

Certain basic compounds of the invention also form pharmaceutically acceptable salts, e.g., acid addition salts and quaternary ammonium salts. For example, when X and/or Y are N or $NR^3$, these nitrogen atoms may form salts, as may the nitrogen atom of the $NR^5$ Z group. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate.

The same nitrogen atoms may also form quaternary salts. The quaternary ammonium salts are prepared by conventional methods, e.g., by reaction of a tertiary amino group in a compound of formula I with a quaternizing compound such as an alkyl iodide, etc. The free base forms differ from their respective salt forms somewhat in certain physical properties, such as solubility in polar solvents, but the salts are otherwise equivalent to their respective free base forms for purposes of the invention.

All such basic and quaternary salts are intended to be pharmaceutically acceptable salts within the scope of the invention and all acid and base salts are considered equivalent to the free forms of the corresponding compounds for purposes of the invention.

It is noted that X and Y may both be $NR^3$. In such instances, the $R^3$ groups may be the same or different. Also, there may be more than one $R^1$ and/or $R^2$ group. In such and similar instances, the multiple $R^1$ and/or $R^2$ groups may be the same or different.

When utilized herein, the terms below, unless otherwise indicated, have the following scope:
halo-represents fluoro, chloro, bromo and iodo;
alkyl (including the alkyl portions of aralkyl and heteroarylalkyl) - represents straight or branched carbon chains which, unless otherwise specified, contain from 1 to 6 carbon atoms;
carbocyclic ring—represents a saturated hydrocarbon ring of from 5 to 8 carbon atoms, e.g. a cycloalkyl group such as cyclopentyl or cyclohexyl, which hydrocarbon ring may be a spiro or fused ring depending on whether the $R^1$ and $R^2$ groups defining the carbocyclic ring are on the same or different carbon atoms, respectively;
aryl (including the aryl portions of aralkyl and aroyl-)—represents a carbocyclic group containing from 6 to 15 carbon atoms and having at least one benzene ring. More preferably aryl is substituted or unsubstituted phenyl or naphthyl Suitable aryl groups include, e.g. phenyl, 1- or 2-naphthyl, indenyl, indanyl, 3-chlorophenyl, 4-chlorophenyl, 4-fluorophenyl, etc.;

heteroaryl (including the heteroaryl portions of heteroarylalkyl and heteroaroyl)—represents cyclic groups having at least one O, S and/or N interrupting a carbocyclic ring structure and having a sufficient number of delocalized pi electrons to provide aromatic character, with the aromatic heterocyclic groups preferably containing from 2 to 14 carbon atoms, e.g., 2-, 3- or 4-pyridyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1,2,4-thiadiazolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, etc., with all available substitutable carbon atoms thereof being intended as a possible point of attachment; and acyl, aroyl and heteroaroyl—represent alkyl-CO-, aryl-CO- or heteroaryl-CO-, respectively, with the proviso that the carbonyl group -CO- of heteroaroyl is attached to a carbon atom of the heteroaryl group.

substituted phenyl or substituted naphthyl—represents a phenyl group substituted with 1 to 5 Q groups or a naphthyl group substituted with 1 to 7 Q groups on any of the available carbon atoms of such phenyl or naphthyl group, wherein each Q is independently selected from halogen, hydroxy, nitro, alkyl, $CH_2OH$, trifluoromethyl, cyano, $N(R^a)_2$, cycloalkyl, alkoxy, alkenyloxy, alkynyloxy, $S(O)_rR^b$, $NHSO_2R^b$, $NHSO_2CF_3$, $NHCOCF_3$, $SO_2$, $SONHR^b$, $SO_2N(R^b)_2$ $COR^c$, $D\text{-}COR^c$ or $NHCOR^d$, and wherein each $R^a$ independently represents H or alkyl, each $R^b$ independently represents alkyl, phenyl or benzyl, $R^c$ represents OH, $NH_2$ or $OR^b$, each $R^d$ represents H, alkyl, alkoxy, $COR^e$, or $NHR^f$, $R^e$ represents OH or alkoxy, $R^f$ represents H or alkyl, D represents alkylene, and r is 0, 1 or 2;

alkenyloxy—represents a straight or branched carbon chain having at least one carbon-carbon double bond and containing from 2 to 6 carbon atoms, said chain being attached to the phenyl or naphthyl ring through an —O— group;

alkynyloxy—represents a straight or branched carbon chain having at least one carbon-carbon triple bond and containing from 2 to 6 carbon atoms, said chain being attached to the phenyl or naphthyl ring through an —O—group; and alkylene—represents a divalent, straight or branched carbon chain having from 1 to 6 carbon atoms.

The following processes A-H below may be employed to produce various compounds of formula I. In these processes $R^1$, $R^2$, $R^3$, $R^4$, $R^5$, X, Y, Z and n are as defined above, unless otherwise indicated.

A. A compound of formula I wherein Z is O and $R^3$ on the $NR^3$ group in ring s is H can be prepared by reacting a compound of formula II with a non-nucleophilic base such as potassium tertiary butoxide, lithium diisopropylamide, lithium bis(trimethylsilyl)amide, etc., to produce a compound of formula Ia:

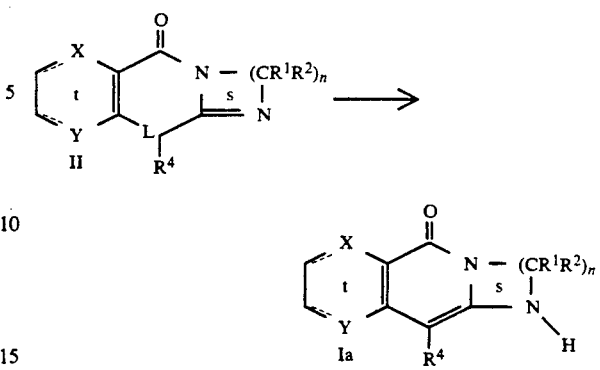

wherein L represents a leaving group such as chloro, methanesulfonyloxy, arylsulfonyloxy, etc. This reaction can be performed at any suitable temperature, e.g., room temperature to reflux, and in any suitable solvent, e.g. tertiary alcohol or ethereal solvent such as tetrahydrofuran (THF), dioxane or diethyl ether.

The compounds of formula II can be easily prepared from compounds known in the art. For example, a compound of formula III can be reacted with a compound of formula IV

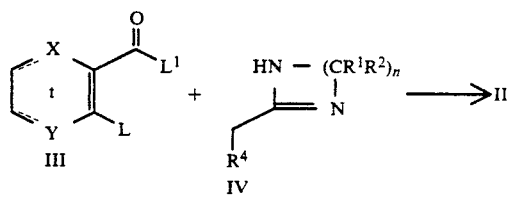

wherein $L^1$ represents a suitable leaving group such as those mentioned above for the group L. This reaction can be performed in any suitable solvent such as halocarbons, ethers, etc., such as dichloromethane, chloroform, THF, etc. and over a range of temperatures from about $-20°$ C. to about $+50°$ C. Compounds of formulas III and IV are known, and are commercially available or easily prepared from known compounds. See, for example, Faust et al., *J. Org. Chem.*, 26, 4044 (1961); German Offen. 2,702,119, corresponding to *Chem. Abstr.*, 87, 167761 (1977); and German Offen 1,117,588, corresponding to Chem. Abstr., 57, 4674 (1962).

B. A compound of formula Ia can be prepared directly by reacting a compound of formula III with a compound of formula IV

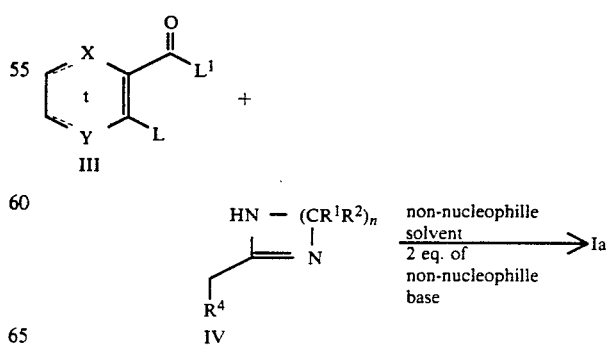

wherein L and $L^1$ are as defined above. Suitable non-nucleophilic solvents include ethereal solvents, halocarbons, hydrocarbons, etc., e.g., THF and dichloromethane. The temperature for this reaction may be essentially as described above for process A. The reaction may be performed in stages by employing first one equivalent of the non-nucleophilic base and allowing the reaction to form a compound of formula II in situ and then adding at least another equivalent of the non-nucleophilic base to complete the reactions.

C. A compound of formula I wherein Z is O and R$^3$ is other than H can be prepared by reacting a compound of formula Ih with a compound of formula V to form a compound of formula Ib

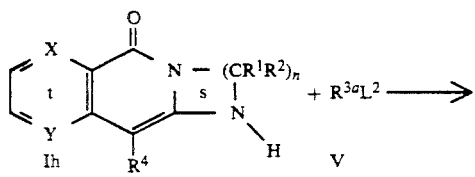

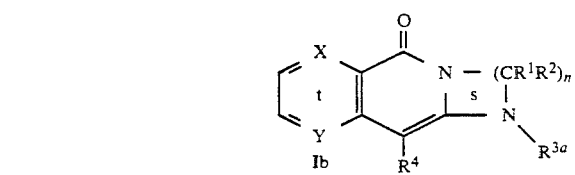

wherein L$^2$ represents a leaving group such as the leaving groups L or L$^1$ as defined above and R$^{3a}$ represents R$^3$ except H. When R$^{3a}$ represents acyl, aroyl or heteroaroyl, the reaction may be performed in the presence of one or more equivalents of a tertiary amine base such as triethylamine or a pyridine-type base, e.g. pyridine itself or lutidine. When R$^{3a}$ is alkyl, aralkyl or heteroaralkyl, the reaction may be performed in the presence of strong base such as NaH, potassium tertiary butoxide, etc. Any suitable solvent for these reactions can be employed. For example, for the acylation reaction, chlorocarbon or ethereal solvent may be used, while with the alkylation reaction a dipolar aprotic solvent such as dimethylformamide can be used.

D. A compound of formula I wherein Z is S can be prepared from a compound of formula Ia or Ib by reaction with P$_2$S$_5$, Lawesson's reagent or the like to produce a compound of formula Ic:

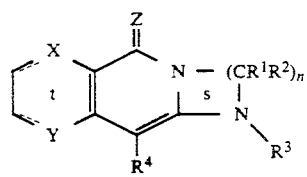

The reaction may take place at elevated temperature in pyridine or other suitable solvent. Lawesson's reagent has the formula:

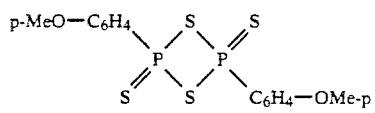

wherein Me is methyl.

E. A compound of formula I wherein Z represents NR$^5$ can be prepared by reacting a compound of formula Ia above or Ij below with an oxaphile such as SOCl$_2$, POCl$_3$, PCl$_3$, PCl$_5$, etc., then with a primary amine of the formula H$_2$NR$^5$.

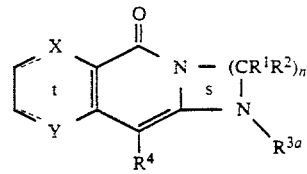

This latter reaction may be carried out in the presence of tertiary amine base such as triethylamine or pyridine.

F. A compound of formula I wherein the dotted lines in ring t both do not both represent double bonds and R$^3$ on the group NR$^3$ in ring s represents R$^{3b}$ which can be H, alkyl, aralkyl, acyl or aroyl can be prepared via a conventional hydrogenation by reacting a compound of formula Id with hydrogen in the presence of a noble metal catalyst such as Pd or Pt, which will selectively hydrogenate the ring t to produce a compound of formula Ie:

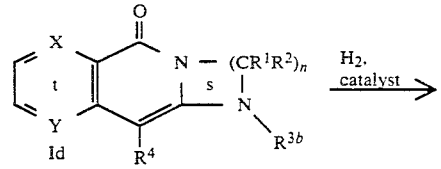

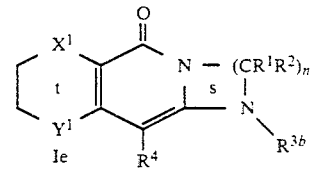

wherein X$^1$ and Y$^1$ independently represent CH$_2$ or NH.

G. The compounds of formula If below wherein R$^{3c}$ is heteroaralkyl or heteroaroyl can be prepared by R$^{3b}$ is H with a compound R$^{3c}$L in the manner as described in general section C above:

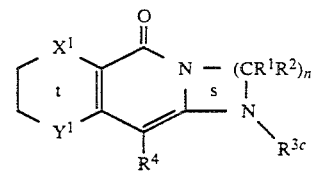

H. The compounds of formula Ig below wherein one or both of Y$^2$ and/or X$^2$ represents NR$^{3a}$ can be prepared by reacting the appropriate compound of formula Ie or If (i.e., one or both of X$^1$ and/or Y$^1$ is NH) with a compound of the formula R$^{3a}$L$^2$ under the conditions described in Section C above.

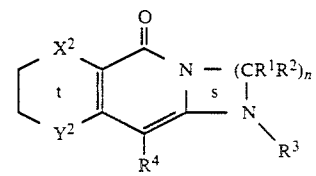

Compounds of the present invention may be of particular utility where a non-steroidal compound is desired which is effective in the treatment of both inflammation and allergies.

The compounds of this invention can be used to treat allergies and their preferred use is for treating allergic chronic obstructive lung diseases. Chronic obstructive lung disease as used herein means disease conditions in which the passage of air through the lungs is obstructed or diminished such as is the case in asthma, bronchitis and the like.

The anti-allergy method of this invention is identified by tests which measure a compound's inhibition of anaphylactic bronchospasm in sensitized guinea pigs having antigen-induced SRS-A mediated broncho-constriction. Allergic bronchospasm was measured in actively sensitized guinea pigs by a modification of the procedure of Konzett and Rossler, *Arch. Exptl. Pathol. Pharmakol.*, 194, pp. 71-74 (1940). Male Hartley guinea pigs were sensitized with 5 mg ovalbumin injected ip and 5 mg injected sc in 1 ml saline on day 1 and 5mg ovalbumin injected ip on day 4. The sensitized animals were used 3-4 weeks later. To measure anaphylactic bronchospasm, sensitized guinea pigs were fasted overnight and the following morning were anesthetized with 0.9 ml/kg ip of dialurethane. The trachea and jugular vein were cannulated and the animals were ventilated by a Harvard rodent respirator. A side arm to the tracheal cannula was connected to a Harvard pressure transducer to obtain a continuous measure of intratracheal pressure. An increase in intratracheal pressure was taken as a measure of bronchoconstriction. Each guinea pig was injected iv with 1 mg/kg propranolol, 5 mg/kg indomethacin and 2 mg/kg mepyramine given together in a volume of 1 ml/kg. Fifteen minutes later, the animals were challenged with antigen (0.5 per cent ovalbumin) delivered as an aerosol generated from a DeVilbiss Model 65 ultrasonic nebulizer and delivered through the tracheal cannula for 30 seconds. Bronchoconstriction was measured as the peak increase in intratracheal pressure occurring within 15 minutes after antigen challenge The results measured as the percent inhibition of the increase in intratracheal pressure with various compounds of the invention given orally 2 hours before antigen challenge in this procedure are set forth below in Table 1. The compounds of the invention were also found to inhibit allergen-induced SRS-A and histamine release from sensitized guinea pig lung tissue.

TABLE 1

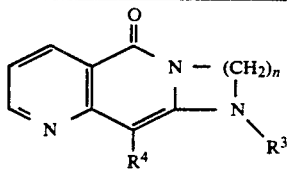

| $R^3$ | $R^4$ | n | Dose (mg/kg p.o.) | % Inhibition of Bronchoconstriction |
|---|---|---|---|---|
| H | phenyl | 2 | 10 | 16 |
| H | 4-methoxyphenyl | 2 | 10 | 8 |
| H | 3-methoxyphenyl | 2 | 5 | 61 |
| H | 3-chlorophenyl | 2 | 5 | 43 |
| H | 4-methylphenyl | 2 | 5 | 1 |

TABLE 1-continued

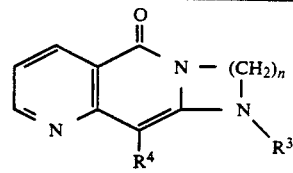

| $R^3$ | $R^4$ | n | Dose (mg/kg p.o.) | % Inhibition of Bronchoconstriction |
|---|---|---|---|---|
| H | 4-chlorophenyl | 2 | 5 | 11 |
| H | 3-chlorophenyl | 3 | 5 | 54 |

The efficacy of compounds of the present invention in the treatment of allergies may be seem by comparison with commercially available compounds. Data for the non-steroidal antihistamine terfenadine, the non-steroidal anti-asthma compound amiophylline and the steroid dexamethasone when administered orally may be found in Table 2 below.

TABLE 2

| Compound | Dose (mg/kg p.o.) | % Inhibition of Bronchoconstriction |
|---|---|---|
| terfenadine | 30 | 5 |
| aminophylline | 18 | 21 |
|  | 53 | 58 |
| dexamethasone | 3 | 38 |
|  | 10 | 46 |

The compounds are effective non-adrenergic, non-anticholinergic antianaphylactic agents. The compounds may be administered by any conventional mode of administration for treatment of allergic reactions employing an effective amount of a compound of formula I for such mode. For example, when administered orally they are active at doses from about 0.2 to 10 mg/kg of body weight; when administered parenterally, e.g., intravenously, the compounds are active at dosages of from about 0.1 to 5 mg/kg body weight; when administered by inhalation (aerosol or nebulizer) the compounds are active at dosages of about 0.1 to 10 mg per puff, one to four puffs may be taken every 4 hours.

The compounds of this invention are also useful for the treatment of inflammation; thus, they are useful for the treatment of: arthritis, bursitis, tendonitis, gout and other inflammatory conditions. The anti-inflammatory use of the compounds of the present invention may be demonstrated by the Reversed Passive Arthus Reaction (RPAR)-PAW technique as set forth below using male Lewis rats (obtained from Charles River Breeding Laboratories) weighing 180-220 grams. The potency of the compounds is determined using indomethacin as the standard. On the basis of the test results, an oral dosage range of about 5 milligrams per kilogram of body weight per day to about 50 milligrams per kilogram of body weight per day in divided doses taken at about 4 hour intervals is recommended, again with any of the conventional modes of administration for treatment of inflammation being suitable.

The dosage to be administered and the route of administration depends upon the particular compound used, the age and general health of the patient and the severity of the inflammatory condition. Thus, the dose ultimately decided upon must be left to the judgment of a trained physician. The antiinflammatory activity may be demonstrated by the following test procedures:

Reversed Passive Arthus Reaction (RPAR) Animals, Materials and Methods

Male Lewis inbred albino rats weighing 180–220 grams obtained from Charles River Breeding Laboratories are used in these experiments. The rats are housed 3 animals/cage and food and water are allowed ad libitum. The animals are numbered 1–3 in each cage and color marked for identification purposes.

All reagents and drugs are prepared just prior to the study. Crystallized and lyophilized bovine serum albumin (BSA), obtained from Sigma Chemical Company, is solubilized without shaking in cold sterile pyrogen free saline (10 mg/ml). Lyophilized anti-bovine serum albumin (IgG Fraction), obtained from Cappel Laboratories, is suspended in sterile distilled water and diluted with cold pyrogen free saline (PFS) just prior to use. The final concentration of anti-bovine serum albumin is 0.5 mg/ml of PFS. Both BSA and anti-BSA solutions are iced during use. Drugs are suspended or solubilized in an aqueous solution of methyl cellulose (MC) with a homogenizer just prior to administration.

Groups of animals (6/group) are dosed with drug in MC by gavage one hour prior to sensitization with BSA. Controls are given MC alone and drug-standard is usually included in each assay for verification purposes. Drugs are prepared so as to provide a dose for a 200 gram animal which is equivalent to the mg/kg dose for the experiment. Thus each rat receives an oral dose in a volume of approximately 2.0 cc. One hour after dosing the animals are lightly anesthetized with ether and sensitized by injecting into the penile vein 0.2 ml of PFS containing 1.0 mg of BSA. One hour later they are injected in the plantar region of one hind paw with 0.1 ml of PFS containing 0.1 mg of the anti-bovine serum albumin. Immediately after the subplantar injection, the injected paw is dipped (up to the lateral maleolus) into the mercury well of a plethysmograph. The volume of mercury displaced is converted to weight and recorded. This value is considered to be the control paw volume for the animal. Paw volumes are also recorded with a plethysmograph during the development of the inflammation at 2 hours post-challenge. The compounds 10-phenyl-2,3-dihydroimidazo[1,2-g][1,6]naphthyridin-5(1H)-one and 10-(4-methylphenyl)-2,3-dihydroimidazo[1,2-g][1,6-naphthyridin-5(1H)-one at doses of 25 mg/kg (p.o.) provided 92% and 42% inhibition, respectively, in this procedure.

Another procedure for testing for acute anti-inflammatory activity measures the reverse passive Arthus reaction in the pleural cavity of rats.

Male Lewis rates weighing 180–220 grams were obtained from Charles River Breeding Laboratories, Wilmington, Mass. and permitted food and water ad libitum. Rooms housing the animals were temperature controlled with a 12 hour light and dark cycle.

Groups of five rats were dosed with drug 30 minutes prior to sensitization with BSA (1 mg/0.2 ml saline). Thirty minutes later the animals were challenged with the IgG fraction of a rabbit anti-bovine serum albumi antibodies (0.1 mg antibody protein per 0.2 ml saline Cooper Biomedical, Malvern, Penna.) in the pleural cavity. Four hours after challenge, the rates were sacrificed and the exudate harvested from the pleural cavity. The volume of the exudate was measured and the total number of cells determined with a Coulter Counter.

$$\% \text{ Inhibition} = 100 - \frac{\text{Control} - \text{Experimental}}{\text{Control}} \times 100$$

The results measured as percent inhibition of the infiltration of polymorphonuclear leucocytes (PMNs) and of eden are set forth below in Table 3.

TABLE 3

Antiinflammatory Activity in the Reverse Passive Arthus Reaction in Rats

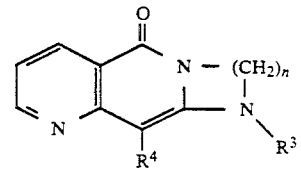

| $R^3$ | $R^4$ | n | Dose (mg/kg p.o.) | Pleurisy (% Inhibition) PMNs | Edema |
|---|---|---|---|---|---|
| H | phenyl | 2 | 25 | 90 | 55 |
|   |   |   | 9 | 54 | 34 |
|   |   |   | 3 | 28 | 25 |
|   |   |   | 1 | 3 | 9 |
| H | 4-methoxyphenyl | 2 | 25 | 49 | 42 |
| H | 3-methoxyphenyl | 2 | 25 | 79 | 69 |
| CH$_3$ | phenyl | 2 | 25 | 69 | 56 |
| H | 4-methylphenyl | 2 | 25 | 53 | 42 |
| H | naphthyl | 2 | 25 | 50 | 28 |
| H | 4-chlorophenyl | 2 | 25 | 95 | 92 |
| H | 3-chlorophenyl | 3 | 25 | 82 | 76 |

Table 4 presents comparative data for prednisone, a commercially available steroid.

TABLE 4

| Reverse Passive Arthus Reaction in Rats Using Prednisone. | | |
|---|---|---|
| Dose (mg/kg p.o.) | Pleurisy (% Inhibition) PMNs | Edema |
| 50 | 42 | 58 |
| 25 | 25 | 44 |
| 12.5 | 20 | 27 |
| 6.25 | 16 | 17 |
| 3.125 | 7 | 2 |

Based on a comparison of Tables 3 and 4, the compounds of Table 3 generally were more effective as antiinflammatory agents at comparable doses than the commercially available steroid of Table 4.

Preferably, for antiinflammatory treatment the compounds of the invention may be administered orally in amounts of from 20 mg to 5 g per day, more preferably, 100 mg to 1 g per day. The dose may vary depending upon the mode of administration, severity of the condition being treated, etc.

The compounds of formula I may also be useful in the treatment of hyperproliferative skin disease, e.g., psoriasis, in mammals, e.g., humans, which may be demonstrated by the Arachidonic Acid Mouse Ear Test as described below.

Arachidonic Acid Mouse Ear Test, Materials and Methods

Charles River, female, CD, (SD) BR mice, 6 weeks old, are caged 8/group and allowed to acclimate 1-3 weeks prior to use.

Arachidonic acid (AA) is dissolved in reagent grade acetone (2 mg/.01 ml) and stored at $-20°$ C. for a maximum of 1 week prior to use. Inflammatory reactions are induced by applying 10 ml of AA to both surfaces of one ear (4 gm total).

Test drugs are dissolved in either reagent grade acetone or aqueous ethanol (only if insoluble in acetone) at the same doses selected by Opas et al., *Fed. Proc.* 43, Abstract 2983, p. 1927 (1984) and Young et al., *J. Invest. Dermatol.* 82, pp. 367-371 (1984). These doses are employed to ensure maximum responses and to overcome any difference in topical absorption which could occur with any drug applied in an aqueous ethanol vehicle. The test drug is applied 30 minutes prior to challenge with AA.

The severity of the inflammation is measured as a function of increased ear weight. A 6 mm punch biopsy is removed 1 hour after AA challenge and weighed to the nearest 0.1 mg. Mean ± standard error and all possible comparisons are made via Duncan's Multiple Range Statistic.

As a result of the topical administration of a compound of formula I, a remission of the symptoms of the psoriatic patient, in most cases, can be expected. Thus, one affected by psoriasis can expect a decrease in scaling, erythema, size of the plaques, pruritus and other symptoms associated with psoriasis. The dosage of medicament and the length of time required for successfully treating each individual psoriatic patient may vary, but those skilled in the art of medicine will be able to recognize these variations and adjust the course of therapy accordingly.

Included within the invention are preparations for topical application to the skin whereby the compounds having structural formula I are effective in the treatment and control of skin diseases characterized by rapid rates of cell proliferation and/or abnormal cell proliferation, e.g., psoriasis.

In a preferred method of treating hyperproliferative skin diseases, a pharmaceutical formulation comprising a compound of formula I, (usually in concentrations in the range of from about 0.001 percent to about 10 percent, preferably from about 0.1 percent to about 5 percent) together with a non-toxic, pharmaceutically acceptable topical carrier, is applied several times daily to the affected skin until the condition has improved. Topical applications may then be continued at less frequent intervals (e.g. once a day) to control mitosis in order to prevent return of severe disease conditions.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents. It can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to about 70 percent of the active ingredient. Suitable solid carriers are magnesium carbonate, magnesium stearate, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring.

Liquid form preparations include solutions, suspensions and emulsions. As an example may be mentioned water or water-propylene glycol solutions for parenteral injection.

Formulations for topical application, e.g., for use in treating hyperproliferative skin diseases, may include the above liquid forms, creams, aerosols, sprays, dusts, powders, lotions and ointments which are prepared by combining an active ingredient according to this inventions with conventional pharmaceutical diluents and carriers commonly used in topical dry, liquid, cream and aerosol formulations. Ointment and creams may, for example, be formulated with an aqueous or oily base with the addition of suitable thickening and/or gelling agents.

Lotions may be formulations with an aqueous or oily base and will, in general, also include one or more of the following, namely, stabilizing agents, emulsifying agents, dispersing agents, suspending agents, thickening agents, coloring agents, perfumes and the like.

Powders may be formed with the aid of any suitable powder base, e.g., talc, lactose, starch, etc. Drops may be formulated with an aqueous base or non-aqueous base also comprising one or more dispersing agents, suspending agents, solubilizing agents, etc.

The topical pharmaceutical compositions according to the invention may also include one or more preservatives or bacteriostatic agents, e.g., methyl hydroxybenzoate, propyl hydroxybenzoate, chlorocresol, benzalkonium chlorides, etc.

The topical pharmaceutical compositions according to the invention may also contain other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Preferably, the pharmaceutical preparation is in unit dosage form.

When administered parenterally, e.g. intravenously, the compounds are administered at a dosage range of about 1-30 mg/kg of body weight in single or multiple daily doses.

The quantity of active compound in a unit dose of preparation may be varied or adjusted from 1 mg to 100 mg according to the particular application and the potency of the active ingredient. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired. The compounds are believed to be non-toxic within the recommended dosage range.

The following examples are intended to illustrate, but not to limit, the present invention.

PREPARATIVE EXAMPLE 1

Dissolve 2-chloro-3-pyridinylcarbonyl chloride (4.69g) in dichloromethane (25 ml), and add the solution to a stirred, cooled (ice bath) solution of 2-(2-chlorophenyl)methyl-imidazoline (4.30g) and diisopropylethylamine (7.69 ml) and dichloromethane (25 ml). Allow the resulting solution to stir 2 hours, then wash it with water, 1 M sodium bicarbonate solution, and with water. Dry the dichloromethane solution, using sodium sulfate, then filter and evaporate the solvent. Crystallize the residue from ethyl acetate to obtain 2-[(2-chlorophenyl)methyl]-1-[(2-chloro-3-pyridinyl) carbonyl]-4,5-dihydro-1H-imidazole, mp 128.5°–130° C.

Use essentially the same procedure as set forth in Preparative Example 1 with other 2-(arylmethyl) imidazolines in place of 2-(2-chlorophenyl)methylimidazoline to prepare the corresponding 1-[(2-chloro-3-pyridinyl)carbonyl]-4,5-dihydro-2-(arylmethyl)-1H-imidazoles listed below:

1-[(2-chloro-3-pyridinyl)carbonyl]-4,5-dihydro-2-(phenylmethyl)-1H-imidazole, oil;

2-[(3-chlorophenyl)methyl]-1-[(2-chloro-3-pyridinyl)carbonyl]-4,5-dihydro-1H-imidazole, oil;

1-[(2-chloro-3-pyridinyl)carbonyl]-2-[(3,4-dichlorophenyl)methyl]-4,5-dihydro-1H-imidazole, oil;

1-[(2-chloro-3-pyridinyl)carbonyl]-4,5-dihydro-2-[(3-methoxyphenyl)methyl]-1H-imidazole, oil;

1-[(2-chloro-3-pyridinyl)carbonyl]-4,5-dihydro-2-[(4-methoxyphenyl)methyl]-1H-imidazole, oil;

1-[(2-chloro-3-pyridinyl)carbonyl]-4,5-dihydro-2-(1-naphthalenylmethyl)-1H-imidazole, mp 148°–151° C., from methanol; and 1-[(2-chloro-3-pyridinyl)carbonyl]-4,5-dihydro-2-[(4-methylphenyl)methyl]-1H-imidazole, oil.

EXAMPLE 1

Add potassium tert.-butoxide (0.928g) to 2-[(2-chlorophenyl)methyl]-1-[(2-chloro-3-pyridinyl)carbonyl]-4,5-dihydro-1H-imidazole (2.57g) suspended in tert.-butanol (25 ml). Reflux the reaction mixture under nitrogen for 5 hours, cool the resulting suspension, and evaporate the solvent Partition the residue between chloroform and water, separate and dry the chloroform solution over sodium sulfate. Filter the dried solution, evaporate the solvent, and crystallize the residue from methanol to give 10-(2-chlorophenyl)-2,3-dihydroimidazo [1,2-g][1,6]naphthyridin-5(1H)-one, mp 295°–297° C. (d).

Use essentially the same procedure as in Example 1 above with the other 1-[(2-chloro-3-pyridinyl)carbonyl]4,5-dihydro-2-(arylmethyl)-1Himidazoles listed in Preparative Example 1 above to prepare are the corresponding 2,3-dihydro-10-arylimidazo[1,2-g][1,6]naphthyridin-5(1H)-ones listed below:

2,3-dihydro-10-phenylimidazo[1,2-g][1,6]-naphthyridin-5(1H)-one, mp 250-253° C. (d), from methanol;

10-(3-chlorophenyl)-2,3-dihydroimidazo[1,2-g]-[1,6]naphthyridin-5(1H)-one, mp 268°–272° C., from N,N-dimethylformamide;

10-(3,4-dichlorophenyl)-2,3-dihydroimidazo-[1,2-g][1,6]naphthyridin-5(1H)-one, mp 223°–224° C., from acetone;

2,3-dihydro-10-(3-methoxyphenyl)imidazo-[1,2-g][1,6]naphthyridin-5(1H)-one, mp 268°–271° C., from acetonitrile;

2,3-dihydro-10-(4-methoxyphenyl)imidazo-[1,2-g][1,6]naphthyridin-5(1H)-one, mp 225°–227.5° C., from methanol;

2,3-dihydro-10-(I-napthalenyl)imidazo-[1,2-g][1,6]naphthyridin-5(1H)-one, mp 225°–227° C., from acetonitrile; and 2,3-dihydro-10(4-methylphenyl)imidazo-[1,2-g][1,6]naphthyridin-5(1H)-one, mp 247°–249° C., from acetonitrile.

EXAMPLE 2

Add a solution of 2-chloro-3-pyridinylcarbonyl chloride (4.4 g) in tetrahydrofuran (55 ml) to a stirred, cooled mixture of 2-(4-chlorophenyl)methylimidazoline (4.9 g), potassium tert.-butoxide (2.8 g) and tetrahydrofuran (200 ml). Use a bath of ice and acetone for cooling. Keep the reaction mixture in the bath for 15 minutes, and then allow it to warm to 20° C. over another 15 minutes. To the warmed mixture, add a second portion (2.8 g) of potassium tert.-butoxide; allow the reaction mixture to stir at 20° C. overnight. Evaporate solvent, partition the residue between chloroform and water, and dry the chloroform solution Use sodium sulfate as a drying agent. Filter the dried solution, evaporate the solvent, and crystallize the residue from acetonitrile to obtain 10-(4-chlorophenyl)-2,3-dihydroimidazo[1,2-g]-[1,6]naphthyridin-5(1H)-one, mp 260°–262° C.

Use essentially the same procedure as set forth in Example 2 above with 1,4,5,6-tetrahydro-2-(3-chlorophenyl)methylpyrimidine to prepare 11-(3-chlorophenyl)-1,2,3,4-tetrahydro-6H-pyrimido[1,2-g]-[1,6]naphthyridin-6-one, mp 262°–262 5° C., from ethanol.

EXAMPLE 3

Reflux a mixture of 2,3-dihydro-10-phenylimidazo-[1,2-g][1,6]naphthyridin-5(1H)-one (5.5 g), acetic anhydride (10 ml), and pyridine (60 ml) for 30 hours. Cool the reaction mixture and evaporate the volatile reagents—i.e., excess pyridine and acetic anhydride. Partition the residue between chloroform and water, and dry, filter, and concentrate the organic solution Chromatograph the residue over silica gel, elute the column with chloroform, and crystallize the eluate from chloroform-petroleum ether to obtain 1-acetyl-2,3-dihydro-10-phenyl-imidazo[1,2-g][1,6]naphthyridin-5(1H)-one, mp 229°–231° C.

EXAMPLE 4

Dissolve 2,3-dihydro-10-phenyl-imidazo-[1,2-g][1,6]naphthyridin-5(1H)-one (2.63 g) in N,N-dimethylformamide (100 ml), and add the solution to a stirred suspension of dimethylformamide (25 ml) and sodium hydride (as a 60% dispersion in mineral oil). Use 0.25 g of the dispersion, and stir the resulting mixture for 1 hour at 25° C. Add methyl iodide (8.5 g), and stir for 15 hours, again at 25° C. Pour the mixture over ice and water (500 g), and extract with dichloromethane. Combine extracts, wash them with water and brine, dry them over magnesium or sodium sulfate, and concentrate them. Crystallize the residue from chloroform-acetone to obtain 2,3-dihydro-1-methyl-10-phenylimidazo[1,2-g]-[1,6]naphthyridin-5(1H)-one, mp 237°-240° C.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound having the structural formula I

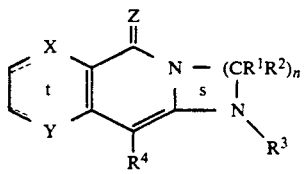

or a pharmaceutically acceptable salt or solvate thereof, wherein:
the dotted lines ---- in ring t either both represent double bonds or such double bonds are absent;
X represents $CH_2$ or $NR^3$ if the dotted line attached thereto does not represent a double bond or CH or N if the dotted line attached thereto represents a double bond;
Y represents $NR^3$ if the dotted line attached thereto does not represent a double bond or N if the dotted line attached thereto represents a double bond;
Z represents O, S or $NR^5$;
n represents an integer 2, 3, 4, or 5;
$R^1$ and $R^2$ may be the same or different and each $R^1$ and each $R^2$ independently represents H or alkyl or two $R^1$ and $R^2$ groups on the same or different carbon atoms may together represent a carbocyclic ring having from 5 to 8 carbon atoms;
each $R^3$ independently represents H, alkyl, aralkyl, heteroarylalkyl, acyl, aroyl or heteroaroyl;
$R^4$ represents H, alkyl, aryl, aralkyl or heteroaryl; and
$R^5$ represents H, alkyl, aryl, heteroaryl, aralkyl, heteroarylalkyl, acyl, aroyl, or heteroaroyl;
wherein alkyl represents straight or branched $C_1$-$C_6$ carbon chains;
aryl represents a carbocyclic group containing from 6 to 15 carbon atoms and having at least one benzene ring;
heteroaryl represents cyclic groups having at least one O, S and/or N interrupting a carbocyclic ring structure;
acyl represents alkyl—CO—;
aroyl represents aryl—CO; and
heteroaroyl represents heteroaryl—CO.

2. A compound according to claim 1 further characterized by:
Z being O or S;
$R^3$ being H or alkyl;
$R^4$ being unsubstituted or mono- or di-substituted phenyl or naphthyl where the substituents are selected from alkyl, alkoxy and halogen; and
n being 2 or 3.

3. A compound according to claim 2 above further characterized by:
Z being O; and
$R^4$ being phenyl, naphthyl or a substituted phenyl where the substituent is selected from 4-methyl, 3-methoxy, 4-methoxy, 3-chloro, 4-chloro and 3,4 di-chloro.

4. A compound according to claim 1 above further characterized by the dotted lines in ring t both representing double bonds.

5. A compound according to claim 1 above further characterized by Y representing N.

6. A compound according to claim 1 above further characterized by X representing CH.

7. A compound according to claim 1 above further characterized by $R^1$, $R^2$ and $R^3$ all being H.

8. A compound according to claim 1 above having the name:
10-(2-chlorophenyl)-2,3-dihydro-imidazo[1,2-g][1,6]-naphthyridin-5(1H)-one;
2,3-dihydro-10-phenyl-imidazo[1,2-g][1,6]naphthyridin-5(1H)-one;
10-(3-chlorophenyl)-2,3-dihydroimidazo[1,2-g][1,6]-naphthyridin-5(1H)-one;
10-(3,4-dichlorophenyl)-2,3-dihydroimidazo[1,2-g][1,6]-naphthyridin-5(1H)-one;
2,3-dihydro-10-(3-methoxyphenyl)-imidazo[1,2-g][1,6]-naphthyridin-5(1H)-one;
2,3-dihydro-10-(4-methoxyphenyl)-imidazo[1,2-g][1,6]-naphthyridin-5(1H)-one;
2,3-dihydro-10-(1-naphthalenyl)-imidazo[1,2-g][1,6]-naphthyridin-5(1H)-one;
2,3-dihydro-10-(4-methylphenyl)-imidazo[1,2-g][1,6]-naphthyridin-5(1H)-one;
10-(4-chlorophenyl)-2,3-dihydroimidazo[1,2-g][1,6]-naphthyridin-5(1H)-one;
11-(3-chlorophenyl)-1,2,3,4-tetrahydro-6H-pyrimido-[1,2-g][1,6]naphthyridin-6-one;
1-acetyl-2,3-dihydro-10-phenyl-imidazo[1,2-g][1,6]-naphthyridin-5(1H)-one;
2,3-dihydro-1-methyl-10-phenyl-imidazo[1,2-g][1,6]-naphthyridin-5(1H)-one;
or a pharmaceutically acceptable salt or solvate of such a compound 9. A pharmaceutically composition comprising an effective amount of a compound of any of claims 1-8 above in combination with a pharmaceutically acceptable carrier.

10. A method for treating allergic reactions, and/or inflammation in a mammal comprising administering to said mammal an effective amount of a compound of formula I as defined in claim 1 above.

* * * * *